United States Patent [19] [11] 3,963,026

Herb [45] June 15, 1976

[54] BLOOD COMPONENT STORAGE BAG AND GLYCEROLIZING SET THEREFOR

[75] Inventor: John R. Herb, Easton, Pa.

[73] Assignee: Pharmachem Corporation, Bethlehem, Pa.

[22] Filed: Nov. 19, 1974

[21] Appl. No.: 525,212

[52] U.S. Cl. ............................ 128/272; 128/214 D; 128/DIG. 24; 150/8; 222/107

[51] Int. Cl.[2] ........................ A61J 1/00; A61M 5/00

[58] Field of Search ......... 128/214 R, 214 D, 214.2, 128/227, 272, 275, 295, DIG. 24; 222/92, 107, 215, 462; 150/8; 215/11 R; 285/158, 423

[56] References Cited

UNITED STATES PATENTS

| | | | |
|---|---|---|---|
| 2,323,629 | 7/1943 | Spanel | 150/8 X |
| 3,105,613 | 10/1963 | Barton et al. | 128/272 X |
| 3,205,889 | 9/1965 | Alder et al. | 128/272 |
| 3,554,256 | 1/1971 | Anderson | 128/214 D X |
| 3,746,001 | 7/1973 | Ralston | 128/214 D |

*Primary Examiner*—Dalton L. Truluck

[57] ABSTRACT

Bag for storing blood components, preferably frozen red blood cells, including an inlet fitment having a neck provided with an enlarged portion on its outer diameter, composed of polyethylene. A novel connection is provided for linking this fitment to a polyvinyl chloride tube, whereby the blood storage bag may be interconnected with a variety of other blood storage or treatment devices.

In the preferred form, the bag is combined with a glycerolizing set consisting of a first flexible resilient polyvinyl chloride tube adapted sealingly to mate with the inlet protrusion of the bag and to communicate with a "Y" connector, which connector further communicates with a glycerin container and with a container of red blood cells.

A novel polyvinyl chloride sleeve structure is provided for securing the polyvinyl chloride tubing firmly on the polyethylene fitment of the bag.

4 Claims, 2 Drawing Figures

BLOOD COMPONENT STORAGE BAG AND GLYCEROLIZING SET THEREFOR

FIELD OF THE INVENTION

This invention pertains to a bag for storing blood components which is readily adaptable to a variety of uses. More particularly, this invention pertains to such a bag in combination with a simple and convenient glycerolizing set.

DISCUSSION OF THE PRIOR ART

Sterilizable, flexible closed plastic bags of a variety of shapes and forms have been used as storage containers for blood and various blood components. In most cases, these bags have been adapted to particular uses by virtue of specific inlet and outlet configurations in combination with puncturable diaphragms and integral tubing adapted to the particular use for which the bag was intended. Undue expense and inconvenience is caused by these prior art bags due to their inherent limitation to the use for which they are intended and their relative non-adaptability to other uses.

CO-PENDING APPLICATION

In my co-pending U.S. application Ser. No. 474,182, filed May 29, 1974, I have disclosed a simple plastic bag adaptable to a number of blood storage uses by virtue of one or more unique inlet fitments.

In that application, I disclosed a storage bag consisting of a sterilizable, flexible closed plastic container with means for hanging the container either in an upright or inverted position, the container further including an inlet-outlet fitment at the top thereof. The disclosed fitment includes an outlet comprising a first hollow outward protrusion with a removable cap and at least one inlet consisting of a second hollow outward protrusion, the second protrusion having on its outer diameter a circumferential raised portion adapted to sealingly engage the inner diameter of flexible tubing whereby the bag is connected with a variety of other blood storage or treatment devices.

In the preferred form of the disclosed invention, this bag is combined with a simple and convenient glycerolizing set the first flexible tube of which sealingly engages the inlet protrusion of the bag and communicates with a Y connector, which in turn communicates through a second resilient flexible tube with a drip chamber attached to a hollow spike for puncturing a container such as a container of glycerin to withdraw fluid therefrom. The Y connector also communicates through a third flexible resilient tube with a second hollow spike, so that the spike may be inserted in a container, such as a container of red blood cells, to permit free fluid passage through the spike into and from the fluid container.

As disclosed in my aforesaid patent application, the drip chamber may consist, for example, of a transparent collapsible cylinder, of substantially larger diameter than the flexible tube in which it is connected, permitting observation of the flow rate of drips or fluid stream through the chamber. The collapsibility of the chamber provides the possibility of using the chamber as a pump by squeezing it and releasing it to cause fluid to be drawn into or forced from the chamber.

With respect to the materials which are used for storage of blood, polyethylene is the material of choice. Other materials such as polyvinyl chloride which have heretofore been used, are now contra-indicated and there is evidence to lead one to believe that polyvinyl chloride may be carcinogenic in nature, particularly when maintained in contact with stored blood over an extended period of time.

Nevertheless, polyvinyl chloride is an ideal material to use for flexible tubing and the like, and it is highly desirable to utilize polyvinyl chloride tubing for conducting the blood and/or the glycerol into the polyethylene storage bag.

However, in actual use of the apparatus of my aforementioned prior patent application, the polyvinyl chloride tubing has sometimes been found to come loose from or to separate from the polyethylene fitment which is formed integrally with the polyethylene bag, with resulting procedural interruption, wastage, etc. In our endeavors to find a way firmly securing the polyvinyl chloride sleeve to the polyethylene fitment, overwhelming difficulties were encountered and for some time it was considered necessary to redesign completely the structure, length and nature of the polyethylene fitment.

It is accordingly an object of this invention to provide a way of securely fitting a polyvinyl chloride tube over an enlarged polyethylene fitment, and for maintaining them together in such a manner that notwithstanding the presence of substantial forces tending to pull the sleeve off of the fitment, to assure that they will remain connected to each other.

BRIEF DISCLOSURE OF THE INVENTION

It has now been discovered that a small, snugly fitted polyvinyl chloride sleeve may be fitted over the expanded head of the polyethylene fitment, so that it is mechanically held beneath the expanded head, that the polyvinyl chloride sleeve may then be slid over the expanded polyethylene head and over the outside surface of the polyvinyl chloride sleeve, and that the polyvinyl chloride sleeve may be adhered to the inner surface of the polyvinyl chloride tubing by merely applying solvent at the interface and permitting it to dry.

DETAILED DESCRIPTION OF THE INVENTION

Figure 2:
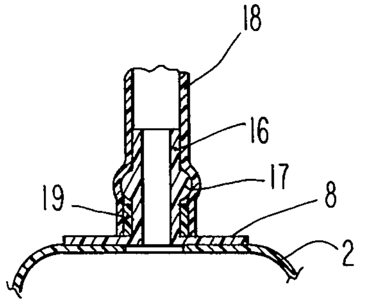
Figure 1:
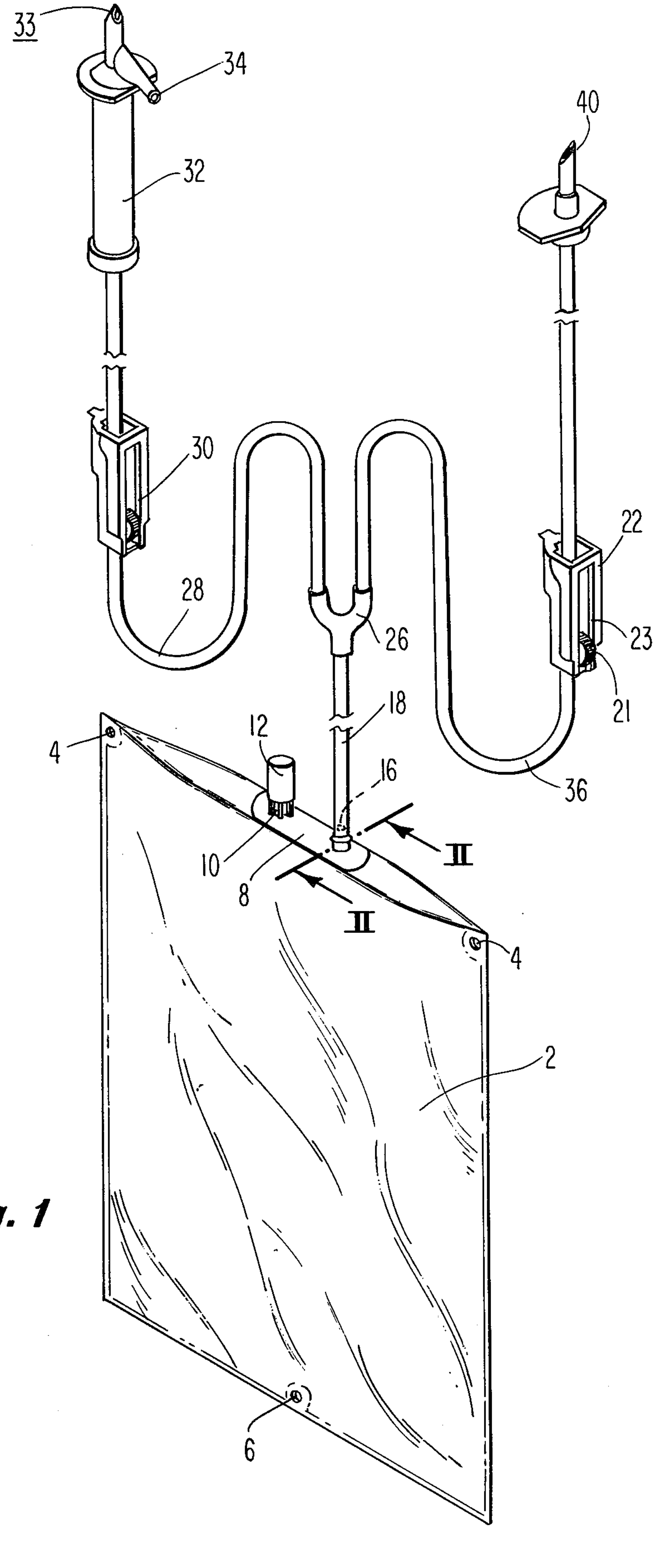

For a better understanding of this invention, reference is made to the appended claims and to the following detailed description thereof, taken in conjunction with the drawings in which:

FIG. 1 is a perspective view of the blood storage bag and associated glycerolizing set of this invention, and FIG. 2 is an enlarged sectional view of the closure fit on the inlet opening of the bag shown in FIG. 1.

Turning now to FIG. 1, there is shown a sterilizable, flexible polyethylene bag 2 with means consisting of hanging holes 4 and 6 for hanging the bag either in an upright or inverted position. Bag 2 also includes a reinforcement 8 including first hollow outward protrusion or neck 10 comprising the outlet opening of the bag. Neck 10 is located over reinforcement 8 in bag 2. A removable outlet cap 12 encloses neck 10, with engagement between cap 12 and sealing ridges 13 providing a protective seal.

The closure fitment integral with reinforcement 8 (as better seen in the enlarged sectional view of FIG. 2) also has a hollow neck 16. Neck 16 also includes a ridge or spherical enlargement 17 on its outer diameter. Closure fitment 8, particularly including necks 10 and 16, provides a convenient and simple means for adapting bag 2 to any of a variety of blood storage applications, including the storage of various blood components and the freeze storage of red blood cells.

As shown in the preferred form of the present invention, neck 16 which is formed of polyethylene sealingly mates with a flexible resilient polyvinyl chloride tube 18, the inner diameter of which corresponds to the outer diameter of a small polyvinyl chloride sleeve 19 stretched over the enlargement 17 and seated thereunder around the base of neck 16 so as to facilitate this sealing engagement of these elements.

Preferably, solvent is applied to the outer surface of sleeve 19 and to the inner surface of the end of tube 18. Since both are composed of polyvinyl chloride, they are solventwelded to each other to form a permanent connection.

As shown, tube 18 is connected to Y conductor 26, the other two legs of which are connected first to second flexible resilient tube 28 having mounted thereon a second valve member 30 providing a controllable fluid flow restrictor as may be required in the functioning or use of the apparatus. Second tube 28 communicates with drip chamber 32, consisting of a relatively large diameter transparent collapsible symmetrical chamber attached to a hollow puncturing spike 33, in which is incorporated an integral air vent 34.

The remaining leg of Y connector 26 is connected to a third flexible resilient tube 36. Tube 36 is connected to a second hollow puncturing spike 40 and fluid flow therein is controlled by means of a valve means 22 with a roller 21 mounted in an inclined channel. A portion of roller 21 protrudes through a lengthwise opening 23 in housing 22.

In the use of the bag and glycerolizing set of the present invention, particularly in the use of the glycerolizing set in conjunction with the use of the bag as a freeze storage container for red blood cells, fluid flow in tube 18 is first restricted by valve means 22 and drip chamber 32 is partially collapsed, such as by squeezing it. Spike 33 is then inserted in a resilient closure cap of a container of glycerin or other suitable red blood cell preservative. Spike 40 is inserted in a container of red blood cells and, with valve means 30 in an open position, the glycerin container is raised or the red blood cell container 2 is lowered so that glycerin enters the red blood cell container 2. After about 100 milliliters of glycerin have passed, valve means 30 is closed. After permitting the partially glycerolyzed red blood cells to equilibrate for 5 to 10 minutes, valve 22 is opened and the contents of the red blood cell storage container are caused to flow by gravity or otherwise into bag 2. Valve means 30 is then opened and the remainder of the glycerin passes into bag 2.

The glycerolyzing set is then sealed (dielectric sealed) approximately one-half inch above the inlet protrusion or neck 16 and the glycerolizing set is then separated from the red cell freezing bag by cutting above the neck 16, whereupon the treated red blood cells in bag 2 are ready for freeze storage.

It will accordingly be seen that it is critical, in the operation and use of the glycerolizing set, to provide an extremely stable but flexible connection between the polyvinyl chloride tube 18 and the polyethylene neck 16. At times the bag 2 may hang by its own weight from such a connection, and it would be highly undesirable to have the connection between the tube 18 and the neck 16 interrupted or broken. In the past, considerable difficulty has been encountered with the tube 18 sliding off the spherical enlargement 17. In accordance with this invention, wherein the auxiliary or supplemental polyvinyl chloride sleeve 19 is stretch-fitted over the enlargement 17 (which similarly compresses concurrently with the stretch-fitting operation), the sleeve 19 is placed in a position where it is firmly secured mechanically beneath the enlargement 17. As will be apparent, the length of the supplemental sleeve 19 should be just about equal to the distance between the base of the enlargement 17 and the surface of the reinforcing portion 8 of the neck 16. In this manner, the supplemental sleeve 19 is firmly secured in its position agianst the base of the neck 16. Just before the operator desires to attach the tube 18 of polyvinyl chloride to the bag, any solvent for polyvinyl chloride (such as methyl-ethyl ketone, acetone, etc.) may be applied around the outer surface of the sleeve 19 and the tube 18 fitted thereover. By mutual solvent action, followed by drying, the inner surface of the tube 18 is "solvent-welded" to the outer surface of the tube 19.

While this invention has been described with respect to specific embodiments thereof, it should be understood that this invention is not limited to these embodiments and that the appended claims are intended to include these and other features and embodiments as may be devised by those skilled in the art which are nevertheless within the spirit and scope of this invention.

The following is claimed:

1. The combination of a bag for storing blood components with a tube member communicating therewith, said combination comprising, a sterilizable, flexible closed container including an inlet therein forming part of said closed container, said inlet being adapted for fluid-tight connection to said tube member through which said blood components are caused to flow, said tube member having an end portion composed of a plastic material which is incompatible for solvent-welding with the material of said inlet, said inlet consisting of a base and a hollow protrusion having on its outer surface an enlarged portion spaced from said base, a sleeve trapped between said enlarged portion and said base, said sleeve being composed of a plastic material which is compatible for solvent-welding with a portion of said tube member, said tube member including a portion compression fitted over said enlarged portion and solvent-welded to said sleeve.

2. Bag for storing blood components, consisting of a sterilizable, flexible closed container includng an inlet at the top thereof forming part of said closed container, said inlet consisting of a base and a hollow protrusion having on its outer surface an enlarged portion spaced from said base, a sleeve trapped between said enlarged portion and said base, and a tube fitted over said enlarged portion and secured to said sleeve, said inlet base and enlarged portion being composed of polyethylene, and both said sleeve and said tube being composed of polyvinylchloride.

3. Bag for storing blood components, as recited in claim 2, further including a solvent-welded joint whereby said sleeve and said tube are solvent-welded to each other.

4. Bag for storing blood components, as recited in claim 3, wherein said solvent-welded joint includes solvent selected from the group consisting of methyl-ethyl ketone and acetone.

* * * * *